United States Patent
Miyake et al.

(10) Patent No.: US 6,514,946 B1
(45) Date of Patent: Feb. 4, 2003

(54) MACROLIDE ANTIBIOTICS AND TREATMENT AND PROPHYLAXIS OF PASTEURELLOSIS USING THE SAME

(75) Inventors: Toshiaki Miyake, Yokohama (JP); Tomohisa Takita, Asaka (JP); Masa Hamada, Tokyo (JP); Tomio Takeuchi, Tokyo (JP); Sumio Umezawa, deceased, late of Tokyo (JP), by Miyoko Umezawa, Asako Wadachi, legal representatives (73) Assignee: Zaidan Hojin Biseibutsu Kagaku Kenkyu Kai, Tokyo (JP)

( * ) Notice: Subject to any disclaimer, the term of this patent is extended or adjusted under 35 U.S.C. 154(b) by 0 days.

(21) Appl. No.: 09/649,038

(22) Filed: Aug. 29, 2000

(30) Foreign Application Priority Data

Aug. 30, 1999 (JP) .......................................... 11-243286

(51) Int. Cl.$^7$ ...................... A61K 31/70; C07H 17/08
(52) U.S. Cl. .......................................... 514/30; 536/7.1
(58) Field of Search ............................... 536/7.1; 514/30

(56) References Cited

U.S. PATENT DOCUMENTS

| | | | | |
|---|---|---|---|---|
| 4,454,314 A | 6/1984 | Nagel | ......................... | 536/7.1 |
| 4,629,786 A | 12/1986 | Debono et al. | .............. | 536/7.1 |

FOREIGN PATENT DOCUMENTS

| | | |
|---|---|---|
| JP | 59-44398 | 3/1984 |
| JP | 59-51299 | 3/1984 |
| JP | 59-167598 | 9/1984 |
| JP | 59-181299 | 10/1984 |
| JP | 59-225199 | 12/1984 |

*Primary Examiner*—James O. Wilson
(74) *Attorney, Agent, or Firm*—Wenderoth, Lind & Ponack, L.L.P.

(57) ABSTRACT

20,23-disubstituted mycaminosyltylonolide derivatives and use of the same in the field of the prophylaxis and treatment of pasteurellosis are disclosed. The di-substituents are peperidino optionally substituted with one or two methyl groups. The derivatives have selective antibacterial activity against Pasteurella.

7 Claims, 1 Drawing Sheet

Fig. 1

MACROLIDE ANTIBIOTICS AND TREATMENT AND PROPHYLAXIS OF PASTEURELLOSIS USING THE SAME

TECHNICAL FIELD

This invention relates to 16-membered ring macrolide antibiotics and the treatment or prophylaxis of pasteurellosis of mammalian livestock or poultry using the same as an active ingredient.

BACKGROUND ART

Some 16-membered ring macrolide antibiotics including tylosin are antibiotic:s which have been used from long ago in treating infectious diseases of humans and livestock. Thereafter, comprehensive derivatives have been proposed aiming to enhance their antibacterial activity and heighten the selectivity of the antibacterial activity. However, the greater part of the various derivatives which have thus been proposed are left alone without attaining their purpose.

Taking infectious diseases with Pasteurella as an example among these infectious diseases, various derivatives showing antibacterial activity against Pasteurella are known, but the derivative being put to practical use is only tilmicosin (or Micotil®), as stated thereinafter.

Tilmicosin (Micotil®)

On the other hand, among the derivatives of tylosin or mycaminosyltylonolide represented by the following formula (A)

(hereinafter, sometimes abbreviated as MT), compounds showing antibacterial activity against *Pasteurella haemolytica* as a main causal bacterium of pasteurellosis are also known, although they are not put to practical use [see Japanese. Laid-open Patent Publication No. 59-167598 (claim of priority: Feb. 28, 1983, U.S. Ser. No. 06/470,833, now abandoned, Japanese Laid-open Patent Publication No. 59-44398 (claim of priority: Aug. 2, 1982, U.S Ser. No. 404024, now U.S. Pat. No. 4,454,314,)]. There is a disclosure in the former publication "Some of the derivatives have activity against certain Gram-negative bacteria of the genus Pasteurella", and it is disclosed that compounds of the formula (A) wherein the aldehyde group at the 20-position and the hydroxyl group at the 23-position are replaced with (i) methyl and octahydroazocin-1-yl and (ii) methylol and octahydroazocin-1-yl, respectively, show an MIC of 0.78 μg/ml against a certain strain of Pasteurella haemolytica. Further, the former publication discloses compounds of the formula (A) wherein the aldehyde group at the 20-position and the hydroxyl group at the 23-position are replaced with pyrrolidin-1-yl and hydroxyl; piperidin-1-yl and hydroxyl; and octahydroazocin-1-yl and octahydroazocin-1-yl, respectively, but there is no specific disclosure on whether these compounds have antibacterial activity against Pasteurella.

Further, as publications describing interesting derivatives proposed by part of the present inventors, although there is no disclosure about antibacterial activity against Pasteurella, Japanese Laid-open Patent Publication Nos. 59-181299, 59-51299 and 59-225199 are mentioned. These publications disclose, for example, compounds of the formula (A) wherein the aldehyde group at the 20-position and the hydroxyl group at the 23-position are replaced with a di-lower alkyl-substituted amino group and inclusively a 5- to 13-membered alkylene-imino group, respectively. Antibacterial activities against Micrococcus, Staphylococcus, Streptococcus, Klebsiella, Shigella and Salmonella of part of these compounds are shown, and it is also described that these compounds have excellent antibacterial activity against Gram-positive and Gram-negative bacteria and are useful as an antibacterial agent.

Bovine respiratory disease as a typical disease among pasteurellosis is a disease from which cattle of all ages may suffer and young animals may generally suffer more easily. Above all, pneumonic pasteurellosis or shippin fever is a disease from which young, stressed cattle suffer in a higher probability. As stated above, tilmicosin is used in the treatment of such diseases, but needs for safely usable and effective drugs still exist. Especially when it is taken into account that such a drug is administered to cattle directed to milking or meat, the provision of a drug which not only has low general toxicity, but also has antibacterial activity as low as possible against bacteria other than bacteria to be controlled (thereby frequency in the emergence of drug-resistant bacteria will be lowered) but strong antibacterial activity against objective bacteria (namely, Pasteurella) will be desired in view of safe use.

DISCLOSURE OF INVENTION

It is known that a compound of the formula (A) wherein the aldehyde group at the 20-position and the hydroxyl group at the 23-position were replaced with alkyleneimino groups, respectively, the compound being inclusively described in the Japanese Laid-open Patent Publication No. 59-181299, generally has excellent antibacterial activity against Gram-negative bacteria. However, it has now been found that compounds represented by the following formula (I) as a result of novel combined selection of the above both groups have, on the one hand, ant bacterial activity against Pasteurella significantly higher than those of tilmicosin and other compounds having structure similar thereto, but have, on the other hand, significantly lower antibacterial activity against other *Staphylococcus aureus, Escherichia coli, Serratia marcescens*, etc.

Therefore, according to the invention, a compound represented by the following formula (I) or a physiologically acceptable acid addition salt thereof having selectively higher antibacterial activity against Pasteurella is provided:

wherein

R₁ and R₂ are the same and represent a group of the

As other embodiments of the invention are also provided a method and a composition for the treatment or prophylaxis of pasteurellosis, especially of livestock and poultry, and further use of a compound represented by the formula (I) or a physiologically acceptable acid addition salt thereof for preparing a composition for the treatment or prophylaxis of pasteurellosis.

The compounds of the formula (I) not only have significantly higher antibacterial activity against Pasteurella than tilmicosin, but also show significant behavior also in in vivo absorption and excretion, and thus have better efficacy against pasteurellosis.

BRIEF DESCRIPTION OF DRAWINGS

FIGS. 1 (A) and (B) are graphs showing the in vivo kinetics of a compound of the invention P-MT and comparative compounds C-9 and tilmicosin. (A) shows the change of drug concentration with time lapse in the serum of a mouse, and (B) shows the change of drug concentration with time lapse in the lung of a mouse. In the figure, the circle (–●–), the triangle (–▲–)and the square (–■–) are data on P-MT, C-9 and tilmicosin, respectively.

BEST MODE FOR CARRYING OUT THE INVENTION

According to the invention are provided three kinds of compounds represented by the formula (I), namely, compounds wherein R₁ and R₂ are the same and groups of the formula (hereinafter, also referred to as P-MT), groups of the formula (hereinafter, also referred to as MP-MT) or groups of the formula (hereinafter, also referred to as DMP-MT). Particularly preferred among these compounds is P-MT.

"Pasteurellosis" in the invention includes pasteurellosis in any animal so long as it is in line with the object of the invention, but as examples, there can be mentioned pasteurellosis of livestock such as cattle, sheep and pigs and poultry such as chickens, turkeys and ducks. However, in view of treating and preventing the later-described pasteurellosis, pasteurellosis of cattle and sheep is particularly contemplated.

Pasteurellosis whose treatment and prophylaxis are particularly contemplated includes primary or secondary diseases such as hemolytic pneumonia or shipping fever with *P. haemolytica* as a main causal bacterium, hemorrhagic septicemia or sometimes shipping fever with *P. multocida* as a causal bacterium, and chronic respiratory disease with *P. gallinarum* as a causal bacterium. The relevancy between each causal bacterium and each disease is just an example, and not limited thereto.

Against such diseases, the compounds of the formula (I) can be used in the form of a free compound or in the form of an acid addition salt. The acid addition salt can be one prepared using any acid so long as the acid addition salt is physiologically acceptable to animals to which it is administered. Not limited thereto, but as such acids, there can be mentioned hydrochloric acid, sulfuric acid, phosphoric acid, formic acid, acetic acid, lactic acid, malic acid, succinic acid, maleic acid, citric acid, tartaric acid, fumaric acid, cholic acid, glutamic acid, aspartic acid, glycolic acid, sorbic acid, lauric acid, stearic acid, methanesulfonic acid, etc. Salt formation reaction can be carried out by mixing a compound of the formula (I) with an acid among the above ones in an appropriate solvent by a method known per se.

A compound of the formula (I) can be produced in a manner similar to a production process of an analogous known compound, but may advantageously be produced according to the later-described process.

As representative ones of embodiments of use of the compounds of the formula (I) against the above diseases, the following ones can be mentioned but not limitedly.

A composition for the treatment or prophylaxis of pasteurellosis which comprises a compound of the formula (I) as an active ingredient and physiologically acceptable diluent(s) or carrier(s).

Use of a compound of the formula (I) for preparing a pharmaceutical preparation for the treatment or prophylaxis of pasteurellosis.

A method for treating or preventing pasteurellosis of the animal needing it which comprises a stage of administering to the animal the pharmaceutical preparation in an amount enough to treat or prevent the pasteurellosis.

As to a method for the administration, appropriate methods can be varied depending on animals, but in the case of large mammals such as cattle or horses, it is suitable to select oral administration, intravenous injection or subcutaneous injection.

As diluents or carriers which can be incorporated in the pharmaceutical preparation, any of natural or synthetic compounds or substances can be used so long as they are generally used as diluents, carriers or lexcipients of animal drugs and meet the object of the invention. Not limited thereto, examples of diluents or carriers which can be selected depending on dosage form are mentioned below. When a liquid medicine is made, pure water, isotonic physiological saline, Ringer's solution, ethyl alcohol and phosphate buffer solution are used and at least one of them and the active ingredient are mixed, and, if necessary, there can also be added liquid oils such as peanut oil, cotton seed oil, safflower oil, sesame oil, olive oil, corn oil and soybean oil and/or polyhydric alcohols such as glycerol, propylene glycol, sorbitol, mannitol, polyethylene glycol and poly (ethylene glycol-2-propylene glycol-2-polyethylene glycol). When a solid preparation is made, saccharides such as lactose, glucose and sucrose, starches such as corn starch and potato starch, cellulose derivatives such as carboxymethylcellulose sodium, ethylcellulose and cellulose acetate, etc. are used and at least one of them and the active ingredient are mixed. Further, an antioxidant can be incorporated in the pharmaceutical preparation so long as it badly influences the antibacterial activity of the active ingredient. As examples of such antioxidants, there can be mentioned ascorbic acid or stabilized derivatives thereof, sodium hydrogensulfate, α-tocopherol, sorbitol, etc.

A compound of the formula (I) (active ingredient) is incorporated in such a pharmaceutical preparation in such a way that an amount enough to treat or prevent pasteurellosis can be attained by one or plural times of administration. The above pharmaceutical preparation can be prepared using a method or means known in the technical field. The active ingredient can occupy 100% by weight to about 5% by weight, preferably 30% by weight to about 10% by weight of the total weight of the pharmaceutical preparation, and the content can be varied depending on the dosage form.

The dose of the active ingredient to animals can appropriately be selected by an expert (e.g., veterinarian) depending on the kinds of animals, age, use purposes (prophylaxis or treatment) and the state of the disease. When subcutaneous injection is made for prophylaxis to young cattle whose age is two weeks old to three months old, the dose can generally be 1 to 10 mg per 1 kg of the body weight per once, and when subcutaneous injection is made for treatment, the dose can be 2 to 20 mg per 1 kg of the body weight per once.

The invention is further specifically described below based on specific test examples and preparation examples.

The operation and effect of the invention can be confirmed by antibacterial activity (MIC), toxicity tests, in vivo kinetics tests on drugs, clinical effect tests, etc.

Compounds of the invention and comparative compounds provided for each test are enumerated below.

Compound A                                    B
(Invention)

P-MT        —CH₂—N⟨piperidine⟩
            (6-membered ring)

MP-MT       —CH₂—N⟨piperidine⟩—CH₃

DMP-MT      —CH₂—N⟨3,5-dimethylpiperidine⟩

(Comparison)

C-1         —CH₂—N(CH₃)₂
C-2         —CH₂—N(n-C₆H₁₃)₂

C-3         —CH₂—N(cyclohexyl)(CH₃)

C-4         —CH₂—N(CH₃)—CH₂—phenyl

C-5         —CH₂—N(CH₂-phenyl)₂

C-6         —CH₂—N⟨pyrrolidine⟩
            (5-membered ring)

C-7         —CH₂—N⟨azepane⟩
            (7-membered ring)

Note) When only one substituent is shown in the table, the substituents at the 20- and 23-poistions are identical.

Test 1; Minimum Inhibition Concentration (MIC)

MIC was measured, based on the standard method of Japan Society of Chemotherapy, on a BHI agar medium (Brain heart-infusion agar, made by Difco Laboratories Inc.(USA)) with respect to Pasteurella and on a Mueller hinton agar medium (Mueller hinton agar, made by Difco, Laboratories Inc.(USA)) with respect to the other test bacteria in both cases according to the double dilution method. The results are shown in the following Table 1.

TABLE 1

| | Antibacterial activity | | | | | | | | | | | | |
|---|---|---|---|---|---|---|---|---|---|---|---|---|---|
| | Test compound (MIC: μg/ml) | | | | | | | | | | | | |
| Test bacterium | P-MT | MP-MT | DMP-MT | Tilmicosin | C-1 | C-2 | C-3 | C-4 | C-5 | C-6 | C-7 | C-8 | C-9 |
| *Staphylococcus aureus* 193 | 3.13 | 1.56 | 3.13 | 0.39 | 50 | 3.13 | 1.56 | 0.39 | 12.5 | 25 | 1.56 | 0.78 | 0.20 |
| *S. aureus* FDA209P | 6.25 | 1.56 | 1.56 | 0.39 | 50 | 6.25 | 1.56 | 0.39 | 12.5 | 12.5 | 1.56 | 0.78 | 0.20 |
| *S. aureus* Smith (virulent strain) | 12.5 | 6.25 | 6.25 | 1.56 | 100 | 6.25 | 3.13 | 6.25 | 50 | 25 | 3.13 | 1.56 | 0.39 |
| *Micrococcus luteus* PCI1001 | 0.78 | 0.78 | 1.56 | 0.20 | 3.13 | 6.25 | 0.78 | 0.20 | 6.25 | 1.56 | 0.20 | 0.20 | 0.10 |
| *Bacillus subtilis* NRRL B-558 | 25 | 25 | 12.5 | 1.56 | 100 | 12.5 | 3.13 | 3.13 | 50 | 50 | 6.25 | 3.13 | 0.39 |
| *Escherichia coli* NIHJ | 3.13 | 6.25 | 6.25 | 25 | 12.5 | >100 | 3.13 | 6.25 | >100 | 6.25 | 1.56 | 1.56 | 0.78 |
| *E. coli* K-12 R-5 | >100 | >100 | >100 | >100 | >100 | >100 | 12.5 | >100 | >100 | >100 | 25 | 1.56 | >100 |
| *Klebsiella pneumoniae* PCI602 | 3.13 | 3.13 | 6.25 | 25 | 25 | >100 | 3.13 | 6.25 | >100 | 12.5 | 0.78 | 3.13 | 0.78 |
| *Shigella dysenteriae* JS11910 | 6.25 | 6.25 | 12.5 | 100 | 50 | >100 | 6.25 | 3.13 | >100 | 12.5 | 1.56 | 0.78 | 3.13 |
| *Salmonella enteritidis* 1891 | 0.78 | 3.13 | 3.13 | 6.25 | 6.25 | >100 | 1.56 | 1.56 | >100 | 3.13 | 0.78 | 0.78 | 0.78 |
| *Enterobacter aerogenes* ATCC13048 | 6.25 | 12.5 | 25 | 100 | 50 | >100 | 12.5 | 12.5 | >100 | 50 | 3.13 | 6.25 | 6.25 |
| *Serratia marcescens* | 100 | 50 | 100 | >100 | >100 | >100 | 50 | 100 | 100 | 100 | 12.5 | 12.5 | 6.25 |
| *Proteus vulgaris* OX19 | 6.25 | 12.5 | 25 | 100 | 100 | >100 | 12.5 | 12.5 | >100 | 12.5 | 3.13 | 6.25 | 3.13 |
| *Pasteurella haemolytica* BBPO101 N791 *1) | 0.39 | 0.39 | 0.39 | 1.56 | 6.25 | 12.5 | 0.39 | 0.39 | 50 | 1.56 | 0.20 | 0.20 | 0.78 |
| *Past haemolytica* BBPO102 N811 *1) | 0.39 | 0.39 | 0.39 | 1.56 | 6.25 | 12.5 | 0.78 | 0.39 | 50 | 1.56 | 0.20 | 0.39 | 0.78 |
| *Past haemolytica* BAPO103 S801 *2) | 1.56 | 3.13 | 1.56 | 50 | 50 | 100 | 6.25 | 6.25 | >100 | 25 | 1.56 | 1.56 | 0.78 |

TABLE 1-continued

Antibacterial activity

| Test bacterium | Test compound (MIC: µg/ml) | | | | | | | | | | | | |
|---|---|---|---|---|---|---|---|---|---|---|---|---|---|
| | P-MT | MP-MT | DMP-MT | Tilmicosin | C-1 | C-2 | C-3 | C-4 | C-5 | C-6 | C-7 | C-8 | C-9 |
| *Past. multocida* BSPO302 No. 6 *3) | 0.39 | 0.39 | 0.78 | 6.25 | 12.5 | 50 | 1.56 | 1.56 | >100 | 6.25 | 0.39 | 0.39 | 0.39 |
| *Past. multocida* BOPO305 M-17 *4) | 0.39 | 0.39 | 0.39 | 6.25 | 6.25 | 50 | 1.56 | 0.76 | >100 | 3.13 | 0.10 | 0.78 | 0.39 |

In the table, *1), *2), *3) and *4) mean strains separated from cattle, poultry, a pig and a sheep, respectively.

It is understood from Table 1 that P-MT, MP-MT and DMP-MT failing within the invention have high antibacterial activity against *Pasteurella haemolytica* and *Pasteurella multocida* which the present inventors conpemplate selectively controlling, but on the other hand, have relatively low antibacterial activity against the other Gram-positive bacteria and Gram-negative bacteria. For example, in comparison with tilmicosin which is used as an agent for treating or preventing pasteurellosis and C-6 (the 20-position and 23-position of the formula (B) are five-membered ring pyrrolidine), P-MT, MP-MT and DMP-MT of the invention have more than about 4-fold better MIC values against Pasteurella. On the other hand, in comparison with C-7 (the 20-position and 23-position of the formula (B) are seven-membered ring hexamethyleneimine) and C-8 (the 20-position and 23-position of the formula (B) are eight-membered ring octahydroxyazocine), P-MT, MP-MT and DMP-MT have significantly higher MIC values (namely, lower antibacterial activities) against bacteria other than Pasteurella, particularly, *Staphylococcus aureus, Micrococcus luteus, E. coli, Shigella dysenteriae* and *Serratia marcescens*.

Test 2: Toxicity Test

A compound of the invention (P-MT) and comparative compounds (tilmicosin, C-7 and C-8) were diluted with physiological saline, respectively, and intravenously or subcutaneously injected to ICR mice (female, 4; weeks old) with 0.25 ml/mouse.

The results are shown below, respectively.

Tilmicosin (comparative compound) (intravenous injection)

| Dose | Weight (g) | Surviving number | Dissection finding |
|---|---|---|---|
| 2.0 mg/mouse | 21.1 | 0/1 | immediate death |
| 1.0 | 21.4 | 0/1 | immediate death |
| 0.5 | 20.5 | 0/1 | immediate death |
| 0.25 | 20.4 ± 0.2 | 3/3 | no abnormality |

P-MT (intravenous injection)

| Dose | Dissection finding |
|---|---|
| 2.0 mg/mouse | immediate death |
| 1.5 | immediate death |
| 0.5 | alive, no abnormal finding |
| 0.25 | alive, no abnormal finding |

P-MT (subcutaneous injection)

| Dose | Dissection finding |
|---|---|
| 4.0 mg/mouse | alive, no abnormal finding |
| 3.0 | alive, no abnormal finding |

-continued

C-7 (intravenous injection)

| Dose | Surviving number | Dissection finding |
|---|---|---|
| 2.0 mg/mouse | 0/2 (immediate death) | no abnormal finding |
| 1.5 | 0/2 (immediate death) | no abnormal finding |
| 0.5 | 1/2 (immediate death) | no abnormal finding |
| 0.25 | 2/2 | no abnormal finding |

C-7 (subcutaneous injection)

| Dose | Surviving number/ number of used animals | Dissection finding |
|---|---|---|
| 4.0 mg/mouse | 0/1 (died after 30 minutes) | no abnormal finding |
| 3.0 | 2/2 | a little decoloring in kidney |
| 2.0 | 2/2 | no abnormal finding |
| 1.0 | 2/2 | no abnormal finding |

C-8 (intravenous injection)

| Dose | Surviving number | Dissection finding |
|---|---|---|
| 4.0 mg/mouse | 0/1 (immediate death) | |
| 2.0 | 0/3 (immediate death) | |
| 1.5 | 0/1 (immediate death) | |
| 1.0 | 3/3 | no abnormal finding |
| 0.5 | 3/3 | no abnormal finding |
| 0.25 | 3/3 | no abnormal finding |

C-8 (subcutaneous injection)

| Dose | Surviving number | Dissection finding |
|---|---|---|
| 4.0 mg/mouse | 2/2 | Sores and alopecia at the administration part |
| 3.0 | 2/2 | Sores and alopecia at the administration part |
| 2.0 | 2/2 | Sores and alopecia at the administration part |
| 1.0 | 2/2 | Sores and alopecia at the administration part |

Test 3: In vivo Kinetics (Absorption and Excretion Test)

The in vivo kinetics of a compound of the invention (P-MT) and comparative tilmicosin and C-9 in mice and cattle were examined.

(1) Test in Mice

Slc ddY male mice (weight 20±1 g) were used. First, 0.2 ml (5 mg/kg: 0.1 mg/mouse) portions of solutions of 0.5 mg/ml of each of P-MT, tilmicosin and C-9 in sterilized purified water were subcutaneously inoculated into groups of mice, each group consisting of 3 mice, at the abdominal part. Then, 0.5, 1, 2, 4, 8, 24, 48 and 72 hours after the drug inoculation, the mice were exsanguinated by the cut of the cervical artery and then the whole lungs were extirpated, and thereby the sera and the lungs were recovered respectively. The mice during the experiment were bred under a temperature of 23±1° C. and a relative humidity of 55±5%, and drinking water and the feed were freely given.

As to the extraction of each drug, the recovered blood was centrifuged to recover the serum and the sera from the three mice on the same concentration of the drug were mixed. Then, the serum was adjusted to pH 8 with 5% sodium bicarbonate solution, and extracted twice with an equal volume of chloroform. As to the recovered lungs, the lungs from the three mice were combined and made into a 5-fold homogenate using 0.5 M phosphate buffer (pH 8.0), and the homogenate was extracted twice with an equal volume of chloroform. Then, each chloroform layer was concentrated under reduced pressure, and the concentrates were dissolved using 400 μl of the mixture of 0.1 M phosphate buffer (pH 8.0)-methanol (9:1), and the concentration of the drug per 1 g of the sample was measured according to bioassay using *Micrococcus luteus* ATCC 9341 as a use strain (amount of the inoculated bacterium: 0.1%).

Figure 1:
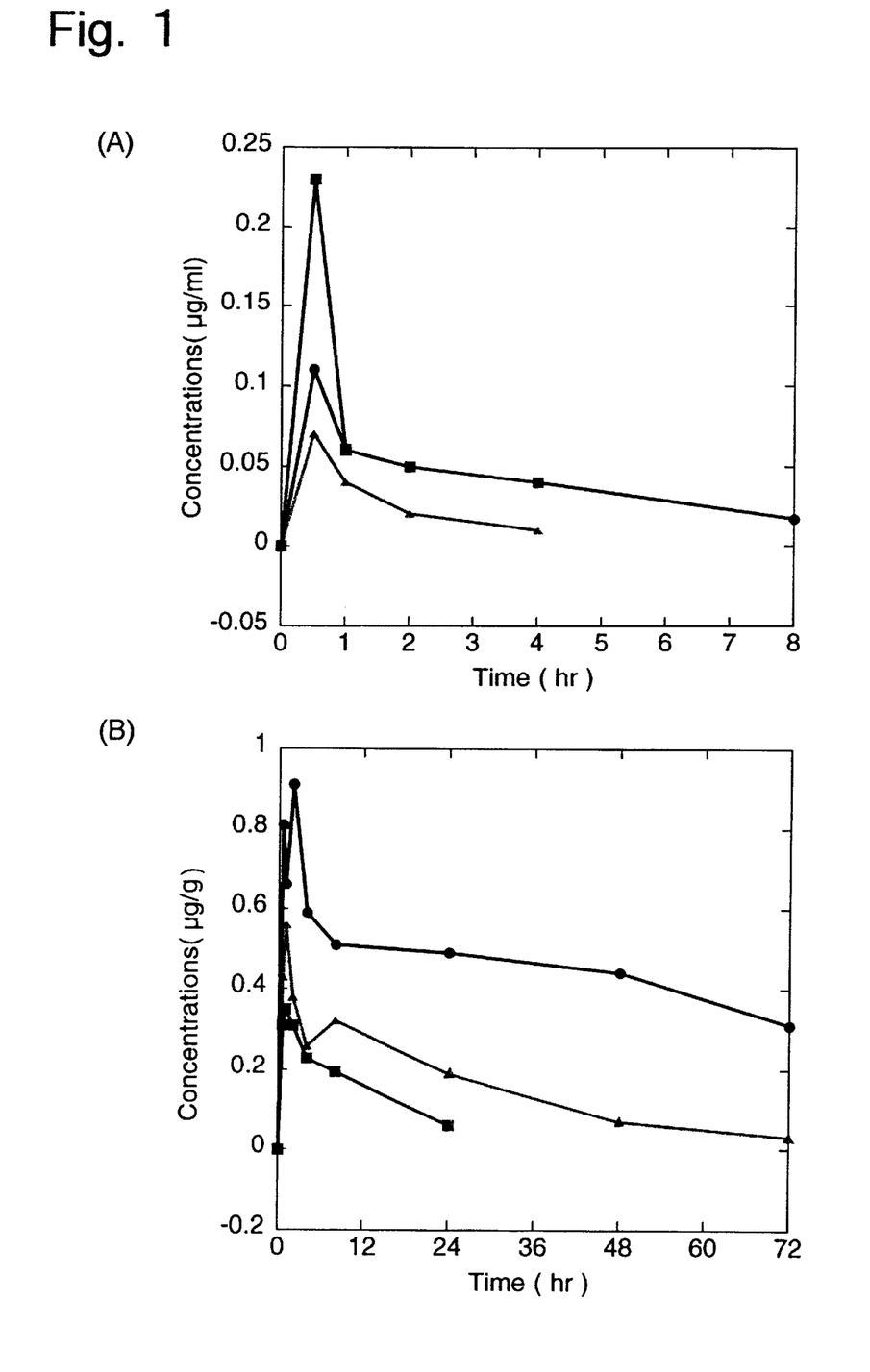

The results are shown in Table 2 and FIG. 1.

calves were bred with a feed not containing any antibacterial substance for two weeks before the administration of a test drug, and as the calves healthy calves which had not been treated with any antibacterial substance were used.

The feed was a milk substitute, and a commercial feed not containing any antibacterial substance was given under such a condition that the same volume is given per calf. Drinking water was given freely. Each drug (10 mg/kg) was dissolved in purified water and subcutaneously administered once to the animal. Before and 0.5, 1, 2, 4, 8, 24, 48, 72 and 120 hours after the administration of the drug, 10 ml or more, of blood was withdrawn from the cervical vein into a vacuum

TABLE 2

Concentration of tilmicosin, C-9 and P-MT in the tissue of mice after 5 mg/kg subcutaneous administration

| Internal organ | Drug | No administration | Concentration in the tissue after each administration time (serum μg/ml, lung μg/g) | | | | | | | |
|---|---|---|---|---|---|---|---|---|---|---|
| | | | 0.5 h | 1 h | 2 h | 4 h | 8 h | 24 h | 48 h | 72 h |
| Serum | P-MT | —* | 0.11 | 0.06 | 0.05 | 0.04 | 0.017 | — | — | — |
| | Tilmicosin | | 0.23 | 0.06 | 0.05 | 0.04 | — | — | — | — |
| | C-9 | | 0.07 | 0.04 | 0.02 | 0.01 | — | — | — | — |
| Lung | P-MT | | 0.81 | 0.66 | 0.91 | 0.59 | 0.509 | 0.49 | 0.44 | 0.31 |
| | Tilmicosin | — | 0.31 | 0.35 | 0.31 | 0.23 | 0.195 | 0.06 | — | — |
| | C-9 | | 0.43 | 0.56 | 0.38 | 0.26 | 0.322 | 0.19 | 0.07 | 0.03 |

*Less than measurement limit

It is understood from Table 2 that as to the concentrations of each drug in the serum and lung after its subcutaneous administration at the murine abdominal part, P-MT of the invention shows the best sustainability and moreover its concentration in the lung is significantly higher than those of the other drugs. It suggests that the compounds of the invention are particularly useful for the prophylaxis and treatment of pneumonic pasteurellosis of the lung and shipping fever.

(2) Test in Cattle

Six one-month-old male suckling calves (Holstein) (weight 42.0 to 71.0 kg, average 54.8 kg) were used. The blood-collecting tube. The plasma was separated by a conventional method divided into two parts, put in preservative vessels, and freezed and preserved at −20° C. The drug was extracted from each plasma according to a conventional method and dissolved in 0.1 M phosphate!buffer (pH 8.0), and the concentration of the drug was measured by a bioassay method using *Micrococcus luteus*. The results are shown in Table 3. It is understood from the table that a compound of the invention P-MT maintains the effective concentration over a longer period than the comparative C-9.

TABLE 3

Change of C-9 and P-MT concentrations in the bovine plasma (μg/mL)

| | Cattle No. | Before administration | Time after the administration | | | | | | | | |
|---|---|---|---|---|---|---|---|---|---|---|---|
| | | | 0.5 | 1 | 2 | 4 | 8 | 24 | 48 | 72 | 120 |
| P-MT administration group | 1 | — | 1.57 | 1.93 | 1.10 | 1.03 | 0.47 | 0.19 | 0.14 | 0.06 | 0.07 |
| | 2 | — | 1.68 | 1.24 | 1.27 | 0.47 | 0.88 | 0.12 | 0.35 | 0.26 | 0.05 |
| | 3 | — | 2.05 | 1.16 | 1.06 | 0.60 | 0.58 | 0.13 | 0.14 | 0.10 | 0.05 |
| | Average | N.C. | 1.77 | 1.44 | 1.14 | 0.70 | 0.64 | 0.15 | 0.21 | 0.14 | 0.06 |
| | Standard deviation | N.C | 0.25 | 0.42 | 0.11 | 0.29 | 0.21 | 0.04 | 0.12 | 0.11 | 0.01 |
| C-9 administration group | 1 | — | 1.67 | 1.02 | 0.70 | 0.62 | 0.36 | 0.11 | 0.05 | — | — |
| | 2 | — | 1.17 | 1.12 | 0.76 | 0.47 | 0.34 | 0.09 | 0.04 | — | — |
| | 3 | — | 1.35 | 0.94 | 0.81 | 0.51 | 0.33 | 0.11 | 0.05 | — | — |
| | Average | N.C. | 1.40 | 1.03 | 0.76 | 0.53 | 0.34 | 0.10 | 0.0 | N.C. | N.C. |
| | Standard deviation | N.C. | 0.25 | 0.09 | 0.06 | 0.08 | 0.02 | 0.01 | 0.01 | N.C. | N.C. |

—: Less than detection limit
N.C.: Not calculated

Test 4: Antiinfective Test on Infected Mice

In this test, *Pasteurella haemolytica* was infected into the abdominal cavity of mice, tilmicosin, C-9 and P-MT were subcutaneously administered at the abdominal part, respectively, and the antiinfective effect of these three drugs against *P. haemolytica* were compared.

(1) Separation and Identification of *P. haemolytica* Having Infectivity to Mice

*P. haemolytica* N791 and N811 (strains distributed from Society of Biological. Preparation for Animals, a corporate juridical person), a strain isolated from the porcine nasal cavity and a strain isolated from the bovine nasal cavity were cultured overnight at 37° C. using tryptosoybouillon (SCD bouillon: Eiken), respectively. Each culture broth was appropriately diluted with sterilized physiological saline and inoculated into the abdominal cavity of DBA/2Cr and ddY male mice using an injection needle. Infectivity was evaluated based on life and death after 7 days of observation. Thus Antiinfective effect was evaluated by breeding and observing the mice for 7 days after the infection and calculating 50% effective dose according to the probit method from the surviving numbers.

The respective sensitivities (MIC) of tilmicosin, C-9 and P-MT against this strain were measured according to the agar plate dilution method in the standard method of Japan Chemotherapy Society (see Chemotherapy 29: 76 to 79, 1981) (preculture: SCD bouillon, measuring medium: 7.5% equine fiber-free blood-supplemented medium for sensitive disks (Nissui), amount of the inoculated bacterium $10^6$ CFU/ml). The results are shown in Table 4. It is apparent from the table that a compound of the invention P-MT has a significantly higher antiinfective effect on the mice infected with *P. haemolytica* than tilmicosin and C-9.

TABLE 4

Antiinfective effect of tilmicosin, C-9 and P-MT on
*P. haemolytica* 63-39 intraperitoneally infected mice

| Drug | MIC ($\mu$g/ml) | Dose (mg/kg) | Surviving number after 7 days/ test number | $ED_{50}$ (95% confidence limit) $ED_{90}$ |
|---|---|---|---|---|
| P-MT | 0.78 | 30 | 10/10 | 4.8 mg/kg (2.7–6.8) |
| | | 20 | 10/10 | 11.0 mg/kg |
| | | 10 | 8/10 | |
| | | 5 | 6/10 | |
| | | 1 | 0/10 | |
| Tilmicosin | 3.13 | 30 | 5/10 | 26.2 mg/kg (16.5–108.3) |
| | | 20 | 4/10 | 102.1 mg/kg |
| | | 10 | 3/10 | |
| | | 5 | 0/10 | |
| | | 1 | 0/10 | |
| C-9 | 1.56 | 30 | 10/10 | 10.3 mg/kg (7.7–13.4) |
| | | 20 | 10/10 | 18.3 mg/kg |
| | | 10 | 3/10 | |
| | | 5 | 1/10 | |
| | | 1 | 0/10 | |
| No treatment | | original liquid | 0/5 | |
| | | original liquid × 1/4 | 3/3 | |

*P. haemolytica* 63-39, a strain isolated from the bovine nasal cavity, was identified as a strain having infectivity to mice. Hereinafter, this 63-39 strain is used. Mice were used Slc ddY male 18.5 to 21 g (weight after 4 days of preliminary breeding).

(2) Test Method

Infection was made by culturing the strain overnight at 37° C. in 100 ml of SCD bouillon and inoculating 0.5 ml portions of the culture broth into the abdominal cavity of the mice using 25G injection needles. Each drug was dissolved in sterilized purified water to give prescribed titer solutions and each group was treated at 5 stages (30, 20, 10, 5 and 1 mg/kg) of drug dose. The administration was made by subcutaneously inoculating 0.2 ml portions of the solutions into the abdominal part one hour after the infection using 26G injection needles, respectively. The bacterial number in the infectious bacteria broth was measured according to a coating method using equine fiber-free blood-supplemented heart infusion agar medium plate. As a result, the bacterial number in the culture broth was $1.2 \times 10^8$ CFU/ml, namely the infected bacterial number being $6.0 \times 10^7$ CFU/mouse.

For the examination of the antiinfective effect groups of mice, each consisting of 10 mice were used, and the mice were bred at a room temperature of 23±1° C. and a relative humidity of 55±5% and drinking water and feed were freely given.

Test 5: Clinical Test Against Bovine Bacterial Pneumonia

In this test, each drug was subcutaneously administered to cattle suffering from bacterial pneumonia (infectious diseases with Mycoplasma, Ureaplasma and Pasteurella), respectively, and the clinical effect of P-MT was compared with those of tilmicosin and C-9.

Tests are made on 17 case of one to two-month-old Holstein cattle (weight 56 to 101 kg) suffering from bacterial pneumonia caused by single or mixed infection of Pasteurella, Mycoplasma, Ureaplasma and Haemophilus (6 animals for each of P-MT and C-9 and 5 animals for tilmicosin). The drug was subcutaneously administered to the animals once a day in an amount of 10 mg/kg. As stated later, it is confirmed by a bacteria isolation test on each animal using nasal cavity swab that the above pneumonia diseases were, specifically, mainly caused by Pasteurella.

Three calves showing a similar degree of symptoms at the start of the test were arranged in one group. Each subject of the same group was respectively tested with one of the above three compounds. Ailing calves were successively grouped when being available.

Clinical findings, based on the daily observation from the time of the administration through the 5th day of the trial, were scored on each item according to the criteria in the table below. The clinical efficacy of the compounds was judged on the 5th day.

|  | Clinical score | | | |
| --- | --- | --- | --- | --- |
| Item/score | 0 | 1 | 2 | 3 |
| Respiration state | Normal | A little quick pulse | Quick pulse | Difficult |
| Respiratory sound | Normal | Weak[a] | Medium[b] | Strong[c] |
| Nasal sap | None | Water-like | Pus-like | — |
| Coughing | None | Sometimes | Frequently | — |
| Vitality | Normal | Reduced | Disappeared | — |
| Appetite | Normal | A little poor | Poor | Vanished |
| Body temperature (under one year old) | At least 38.5° C. and lower than 40.0° C. | At least 40.0° C. and lower than 40.5° C. | At least 40.5° C. and lower than 41.5° C. | Lower than 38.5° C. or 41.5° C. or more |

[a] Abnormal respiratory sound is heard at part of the lung.
[b] Strong bronchial respiratory sound and pulmonary alvelus sound are heard.
[c] Strong Russell sound is heard.

As to judgment based on the clinical symptoms, cases which could be judged among each group were classified into remarkably effective (85 to 100), effective (70 to under 85), a little effective (50 to under 70) and infective (under 50) according to the following improvement rate by clinical scores, and after summing up, the following effective rate was calculated, the difference in the effective rate among the groups was determined using a statistical method, and thus effectivity was judged.

$$\text{Improvement rate} = \frac{\text{Score before administration} - \text{Score 4 days after administration}}{\text{Score before administration}} \times 100$$

$$\text{Effective rate} = \frac{\text{Number of remarkably effective cases} + \text{Number of effective cases}}{\text{Number of cases capable of being judged}} \times 100$$

The change of the clinical scores, the improvement rate and the effective rate, and the results of effect judgment are shown in Tables 5-1, 5-2 and 5-3, respectively.

TABLE 5-1

Change of average clinical score

| Test group | At administration | Days after completion of administration | | | |
| --- | --- | --- | --- | --- | --- |
| | | 1 | 2 | 3 | 4 |
| P-MT | 7.7 | 5.3 | 3.8 | 3.2 | 1.8 |
| C-9 | 7.5 | 3.3 | 2.5 | 2.0 | 1.8 |
| Tilmicosin | 6.5 | 3.5 | 2.8 | 2.2 | 2.7 |

TABLE 5-2

Average symptomatic improvement rate (%) and effective rate (%) in clinical effect

| Test group | Average symptomatic improvement rate (%) | Effective rate (%) in clinical effect |
| --- | --- | --- |
| P-MT | 79.4 | 67 |
| C-9 | 75.9 | 50 |
| Tilmicosin | 65.6 | 40 |

Symptomatic improvement rate:
(Score before administration − Score two days after administration) / (Score before administration) × 100
Effective rate (%) in clinical effect:
(remarkably effective case number + effective case number) / test case number × 100

TABLE 5-3

Judgment of clinical effect

| Test group | Remarkably effectivt (%) (case number) | Effective (%) (case number) | A little effective (%) (case number) | Ineffective (%) (case number) |
| --- | --- | --- | --- | --- |
| P-MT | 67 (4) | 0 (0) | 17 (1) | 17 (1) |
| C-9 | 17 (1) | 33 (2) | 50 (3) | 0 (0) |
| Tilmicosin | 40 (2) | 0 (0) | 20 (1) | 40 (2) |

The results of the bacteria separation test from the nasal cavity swab on the test animals before and after the drug administration are shown in Table 6.

TABLE 6

State of bacteria separation from nasal cavity

| Test group | | Separation rate (%) before administration (number of animal) | Separation rate (%) at completion (number of animal) |
| --- | --- | --- | --- |
| P-MT | P. multocida | 83 (5/6) | 0 (0/6) |
| | P. haemolytica | 50 (3/6) | 0 (0/6) |
| | H. somnus | 17 (1/6) | 0 (0/6) |
| | M. bovis | 67 (4/6) | 67 (4/6) |
| | M. bovirhinis | 50 (3/6) | 50 (3/6) |
| | Urea | 100 (6/6) | 83 (5/6) |
| C-9 | P. multocida | 100 (6/6) | 50 (3/6) |
| | P. haemolytica | 17 (1/6) | 17 (1/6) |
| | H. somnus | 0 (0/6) | 0 (0/6) |
| | M. bovis | 33 (2/6) | 33 (2/6) |
| | M. bovirhinis | 67 (4/6) | 33 (2/6) |
| | Urea | 100 (6/6) | 33 (2/6) |
| Tilmicosin | P. multocida | 100 (5/5) | 80 (4/5) |
| | P. haemolytica | 20 (1/5) | 20 (1/5) |
| | H. somnus | 0 (0/5) | 0 (0/5) |
| | M. bovis | 40 (2/5) | 40 (2/5) |
| | M. bovirhinis | 60 (3/5) | 60 (3/5) |
| | Urea | 100 (5/5) | 60 (3/5) |

P.: Pasteurella
H.: Haemophilus
M.: Mycoplasma
Urea: Ureaplasma

During the treatment, abnormality such as side effect thought to be due to the drug administration was not observed in the subjects.

It is apparent from Tables 5-1 to 5-3 that a compound of the invention P-MT has significantly better efficacy than comparative C-9 and, particularly, tilmicosin practically used now against pasteurellosis of livestock, on the average symptomatic improvement rate (%) and the effective rate (%) in clinical effect and "remarkably effective (%)" in the judgment of clinical effect gotten from the average clinical scores during 5 days after the administration. It is noteworthy that according to the data of Table 6, among the cattle to which a compound of the invention P-MT was administered, *P. multocida* and *P. haemolytica* have come to be not isolated at all, whereas when the comparative compounds were administered, animals from which,; these strains could be isolated exist in both occasions although the number is a few. When animal are put in such a state that they swarm such as, for example, when the shipping fever of cattle needs to be prevented and treated, it will particularly be needed to combat the objective bacteria surely and completely. It is suggested, for example from Table 6, that the compounds of the invention can advantageously be used also for such combating.

PREPARATION EXAMPLE 1

Preparation of P-MT

First, 20,23-diiodo-20,23-dideoxy-20-dihydromycaminosyltylonolide (50.0 mg, 0.0610 mmol) was dissolved in acetonitrile (1 ml), piperidine (0.06 ml, 0.610 mmol) was added, and reaction was made at 80° C. In TLC at 1 hour thereafter the raw materials were not detected at all. The reaction solution was concentrated, and the residue was purified by silica gel column chromatography ($CHCl_3$:$CH_3OH$:28% $NH_3$ water=15:1:0.1) to obtain 43.2 mg (97%) of pale yellow solid of Compound 10. FAB-MS m/z 734 [$(M+1)^+$]. $[\alpha]_{D}^{22}$=+2.40° (c1, $CHCl_3$).

PREPARATION EXAMPLES 2 to 7

Preparation of MP-MT, DMP-MT, C-3, C-4, C-6 and C-7

The same reaction as in Preparation example 1 was repeated except that 4-methylpiperidine (preparation of MP-MT), 3,5-dimethylpiperidine (preparation of DMP-MT), N-methylcyclohexylamine (preparation of C-3), N-methylbenzylamine (preparation of C-4), pyrrolidine (preparation of C-6) and hexamethyleneimine (preparation of C-7) were used respectively in place of piperidine of Preparation example 1 to obtain the captioned compounds, respectively (on the compounds represented by abbreviations, see, if necessary, the description on the formula (B)). Physical properties of the compounds were as follows.

Compound MP-MT: FAB-MS m/z 762 [$(M+1)^+$] $[\alpha]_{D}^{22}$=+2.9° (c1, $CHCl_3$)

Compound DMP-MT: FAB-MS m/z 790[$(M+1)^+$] $[\alpha]_{D}^{22}$=+3.5° (c1, $CHCl_3$)

Compound C-3: FAB-MS m/z 790[$(M+1)^+$] $[\alpha]_{D}^{16}$=+1.1° (c1, $CHCl_3$)

Compound C-4: FAB-MS m/z 806[$(M+1)^+$] $[\alpha]_{D}^{16}$=−1.3° (c1, $CHCl_3$)

Compound C-6: FAB-MS m/z 706[$(M+1)^+$] $[\alpha]_{D}^{23}$=+2.1° (c1, $CHCl_3$)

Compound C-7: FAB-MS m/z 762[$(M+1)^+$] $[\alpha]_{D}^{23}$=+2.5° (c1, $CHCl_3$)

What is claimed is:

1. A compound represented by the formula (I) or a physiologically acceptable acid addition salt thereof:

wherein $R_1$ and $R_2$ are the same and represent a group of the formula

2. A composition for the treatment of pasteurellosis, which comprises a compound represented by the formula (I) or a physiologically acceptable acid addition salt thereof:

wherein

$R_1$ and $R_2$ are the same and represent a group of the formula and a physiologically acceptable diluent or carrier.

3. The composition according to claim 2, wherein the pasteurellosis is pneumonic pasteurellosis or shipping fever.

4. A method for treating pasteurellosis in livestock or poultry, which comprises administering to livestock or poultry infected with Pasteurella a therapeutically effective amount of a compound represented by the formula (I) or a physiologically acceptable acid addition salt thereof:

wherein

R₁ and R₂ are the same and represent a group of the formula

5. The method according to claim 4 wherein the livestock or poultry is selected from: the group consisting of cattle, sheep and pigs.

6. The method according to claim 4 wherein the livestock or poultry is selected from the group consisting of cattle, sheep and pigs, and the pasteurellosis is pneumonic pasteurellosis or shipping fever.

7. The method according to claim 4 wherein the administration is made by intravenous or subcutaneous injection.

* * * * *